United States Patent [19]

Rockliff

[11] 4,347,550
[45] Aug. 31, 1982

[54] SENSOR DETECTOR ELEMENT FOR AN ELECTRICAL HYGROMETER

[76] Inventor: Peter Rockliff, 45, Heath Dr., Boston Spa, Yorkshire, England

[21] Appl. No.: 153,902

[22] Filed: May 28, 1980

Related U.S. Application Data

[63] Continuation-in-part of Ser. No. 863,472, Dec. 22, 1977, abandoned.

[51] Int. Cl.³ .............................................. H01G 7/00
[52] U.S. Cl. .................................. 361/286; 73/336.5; 219/209; 361/322
[58] Field of Search ............... 73/336.5; 361/322, 286; 219/209

[56] References Cited

U.S. PATENT DOCUMENTS 3,220,880 11/1965 Ieversanger ......................... 361/322
4,143,177 3/1979 Kovac et al. .................. 73/336.5 X

FOREIGN PATENT DOCUMENTS 2254977 5/1973 Fed. Rep. of Germany ...... 361/286
805051 11/1958 United Kingdom .

OTHER PUBLICATIONS

Channon, "A Thick Film Humidity Sensor", Conf. on Hybrid Microelectronics, Loughborough, Leics, England, 9/75.

Primary Examiner—Elliot A. Goldberg
Attorney, Agent, or Firm—Harrington A. Lackey

[57] ABSTRACT

A strictly capacitive sensor for an electrical hygrometer comprises an electrode in the form of a slice of doped silicon supporting a dielectric layer of hygroscopic material which in turn supports a further and permeable electrode, while the surface of the silicon which supports the dielectric layer is oxidized to provide an impermeable barrier layer which prevents the sensor acting resistively.

3 Claims, 2 Drawing Figures

SENSOR DETECTOR ELEMENT FOR AN ELECTRICAL HYGROMETER

CROSS-REFERENCE TO RELATED APPLICATION

This is a continuation-in-part of application Ser. No. 863,472, filed Dec. 22, 1977, now abandoned.

This invention relates to a sensor or detector element of an electrical hygrometer of the so-called capacitance type and is intended particularly though not exclusively for meteorological purposes.

In recent years attempts have been made to measure atmospheric humidity accurately and at high speed in the field of Meteorology. Hygrometers of the hair type in the early days have given way recently to electronic devices such as the aluminium oxide sensor. The aluminium oxide sensor has the required sensitivity, but the moisture absorbed by the aluminium oxide renders it electrically conductive and causes the hygrometer to operate otherwise than purely capacitively. Moreover, it has the disadvantage of suffering deterioration over a period of storage and also the disadvantage of being difficult to heat to prevent saturation when exposed to sudden high humidities at low temperatures. The requirement for a very fast, stable, heated sensor has become manifest, as the possibility of using dropsondes (meteorological monitoring devices to be dropped from aircraft) is being examined. The dropsonde starts its journey from a high altitude (approx. 30,000 ft.) where temperatures are low, humidity is low, and atmospheric pressure is low. Falling at great speed the response to changes of humidity has to be very fast. If the sensor were unheated, the first cloud layer encountered would probably produce saturation conditions, and the sensor upon becoming saturated would probably remain saturated due to the very low temperature encountered at high altitudes.

The chief object of the present invention is to provide a new or improved sensor or detector element suitable for meteorological and for industrial use.

According to the invention there is provided a detector element of capacitance type for use in an electrical hygrometer comprising;
(a) a substrate of silicon doped to render it electrically conductive and able to act as a first electrode, and thermally oxidised to produce on at least one surface a thin moisture-impermeable barrier layer of silicon oxide;
(b) a dielectric layer of insoluble hygroscopic material upon and supported by the barrier layer on said one surface; and
(c) a moisture permeable second electrode upon and supported by the dielectric layer.

DESCRIPTION OF THE PREFERRED EMBODIMENTS

Figure 1:
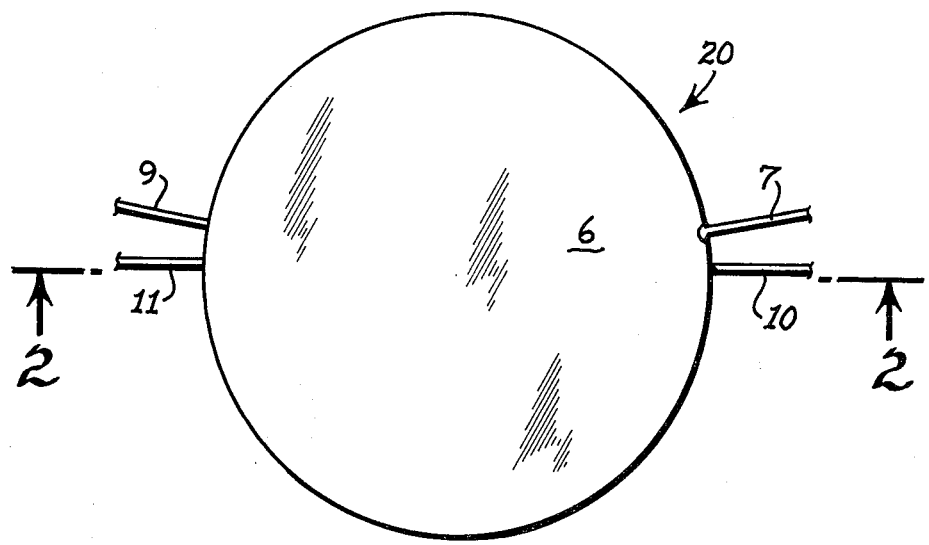
FIG. 1 is a top plan view of one embodiment of a sensor detector element made in accordance with this invention.

In a first embodiment, a disc of silicon 1 which has been doped to render it electrically conductive is used as a support on which to deposit successive layers to form a moisture sensitive device 20. The disc is in the order of 15–16 m.m. diameter and 0.003"–008" thick, although thickness is not critical. The object of the successive layers is to produce a moisture sensitive capacitor rather than a resistive device, as tests over a period of years have established that a capacitive device is more stable than a device of which the resistance changes with moisture changes.

The disc 1 is subjected to thermal oxidation by heating it to a temperature about 1000° C. and passing moistened nitrogen gas over its surface until an oxide layer 2 of sufficient impermeability has been formed. The process is slow, it taking some 5 hours to produce an oxide layer of 6000 A, and in consequence an accurate control of the end point of the process can be achieved.

The object of the oxide layer 2 is to eliminate conductivity between the electrodes by preventing the penetration of water to the surface of the doped silicon base.

In practice, oxide forms on the whole surface of the disc to form layers 2 and 3 covering the opposed faces, and an edge layer 4. To one of the faces covered by the layer 2 is then applied by vacuum coating a thin layer 5 of calcium fluoride to act as the hygroscopic dielectric of the element. In another embodiment of the invention the calcium fluoride layer 5 is replaced by a thin layer of aluminium, again deposited by a known vacuum coating technique, which aluminum is then completely converted to oxide by anodisation.

A gold layer 6 is then deposited by vacuum coating onto the dielectric layer. The gold layer 6, which forms a second electrode 5 is very thin and sufficiently porous to allow the passage of water vapour from the environment to the hygroscopic dielectric 5.

A connection 7 for an electrical hygrometer is made from the gold electrode 6.

The face of the doped and oxidised silicon disc opposed to that on which the hygroscopic layer 5 is formed is, in one embodiment of the invention, then cleaned of its oxide coating by treatment with an acid vapour. The cleaned surface is subsequently vacuum coated with gold to provide for the attachment of a connector to the electrical hygrometer and to improve the effectiveness of the silicon base as an electrode.

Figure 2:
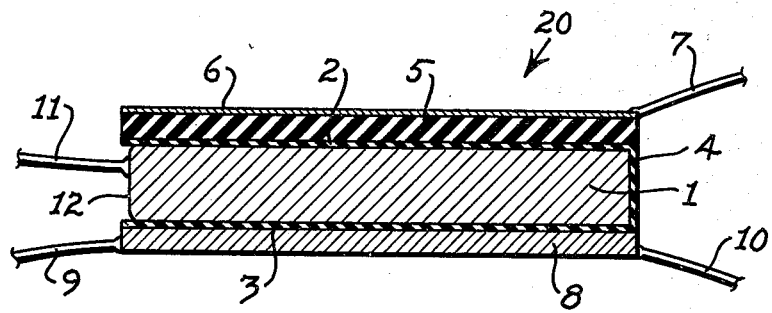
FIG. 2 is a section taken along the line 2—2 of FIG. 1.

The doped silicon may, however, act as an electrode without the addition of a gold layer, and in another embodiment (FIGS. 1 and 2) the oxide layer 3 is not removed from the face opposed to the hygroscopic layer 5, but is itself provided with a thin layer 8 of electric resistance material such as Nichrome or Cermet, e.g. a mixture of silicon monoxide and chromium. This layer 8 is provided with electrical contacts 9 and 10 whereby it may be connected to a source of electric potential of the order of 1.5 to 3 volts in order resistively to heat up the layer 8 and consequently the whole detector element. In this embodiment, an electrical connection 1 with the doped silicon 1 may be made with the edge 12 of the disc after the removal therefrom of any oxide.

The element 2 according to the invention is not restricted to the specific materials mentioned above. For instance, the gold used for the electrodes could be replaced by chromium, or any metal which is resistant to oxidation, although the noble metals do have ideal properties.

The hygroscopic layer 5 could consist of almost any hygroscopic substance which can be vacuum deposited with the exception of hygroscopic water-soluble (i.e. deliquescent) substance.

Whilst the element 20 has been described as being made in the form of a disc, other shapes may be used. In particular for improved commercial production the detectors may be produced in batches (say 25 or 100) on one single slice of silicon and subsequently divided into individual elements by any suitable method e.g. by scoring along a straight line or lines and breaking along the score line(s).

I claim:

1. A detector element of capacitance type for use in an electrical hygrometer comprising:
   (a) a first electrode comprising a substrate of silicon doped to render it electrically conductive and having at least one surface,
   (b) at least said one surface being thermally oxidized to produce a thin, moisture-impermeable barrier layer of silicon oxide,
   (c) a dielectric layer of insoluble hygroscopic material upon and supported by said barrier layer on said one surface,
   (d) a moisture permeable second electrode upon and supported by said dielectric layer, and
   (e) said moisture-impermeable barrier layer of silicon oxide effectively eliminating electrical conductivity between said first and second electrodes, and causing said electrodes to function strictly capacitively.

2. The invention according to claim 1 further comprising a layer of electrically conductive material connectible to a source of electric potential, and supported upon, but electrically insulated from, a surface of said substrate opposed to said one surface, said layer of electrically conductive material constituting an electrically resistive heater for heating the detector element.

3. The invention according to claim 1 further comprising a plurality of said detector elements, said silicon doped substrates forming a single sheet having means for dividing said sheet into individual substrates.

* * * * *